United States Patent [19]
Nitzsche et al.

[11] Patent Number: 5,868,793
[45] Date of Patent: Feb. 9, 1999

[54] METHODS AND APPARATUS FOR IMPROVED TACHYCARDIA DISCRIMINATION IN AN ACTIVE MEDICAL DEVICE

[75] Inventors: Remi Nitzsche, Gambais; Jean-Luc Bonnet, Montrouge; Nicolas Iscolo, Saint Cyr L'Ecole; Marcel Limousin, Montrouge; Christine Henry, Paris; Daniel Kroiss, Schweighouse, all of France

[73] Assignee: ELA Medical S.A., Montrouge, France

[21] Appl. No.: 956,557

[22] Filed: Oct. 23, 1997

[30] Foreign Application Priority Data

Oct. 25, 1996 [FR] France ................................ 96 13083

[51] Int. Cl.⁶ .................................................... A61N 1/39
[52] U.S. Cl. .............................................. 607/5; 600/518
[58] Field of Search ................................ 600/518; 607/5, 607/13

[56] References Cited

U.S. PATENT DOCUMENTS

| | | | |
|---|---|---|---|
| 5,350,406 | 9/1994 | Nitzsche et al. | 600/518 |
| 5,462,060 | 10/1995 | Jacobson et al. | 128/702 |

FOREIGN PATENT DOCUMENTS

| | | | |
|---|---|---|---|
| 0 550 344 | 7/1993 | European Pat. Off. | A61N 1/39 |
| 0 617 980 | 10/1994 | European Pat. Off. | A61N 1/368 |
| 0 626 182 | 11/1994 | European Pat. Off. | A61N 1/368 |
| WO 92/09331 | 6/1992 | WIPO | A61N 1/368 |
| WO 93/02746 | 2/1993 | WIPO | A61N 1/368 |

*Primary Examiner*—William E. Kamm
*Attorney, Agent, or Firm*—Orrick, Herrington & Sutcliffe, LLP

[57] ABSTRACT

An active implantable medical device of the defibrillator/cardiovertor type with an improved tachycardia discrimination for utilizing the delivery of a therapy of defibrillation and/or cardioversion and/or antitachycardia stimulation in the ventricle and/or atrium. The atrial and ventricular activity is monitored, and suspected tachycardia episodes in the monitored activity is tested and confirmed, the stability of RR intervals and the stability of associated PR interval are analyzed. The classification discriminates tachycardias detected as between ventricular tachycardias and supra-ventricular tachycardias, and authorizes delivery of a shock therapy in the presence of a confirmed ventricular tachycardias, or inhibits delivery of a shock therapy in response to a confirmed supra-ventricular tachycardia. Where appropriate, the classification also releases an atrial therapy. The improvement concerns determining the presence or the absence of a rapid acceleration of the rhythm of RR intervals, and determining, if necessary, the origin (atrial or ventricular) of such acceleration, in the case of the detection of unstable RR intervals for discriminating tachycardias.

9 Claims, 2 Drawing Sheets

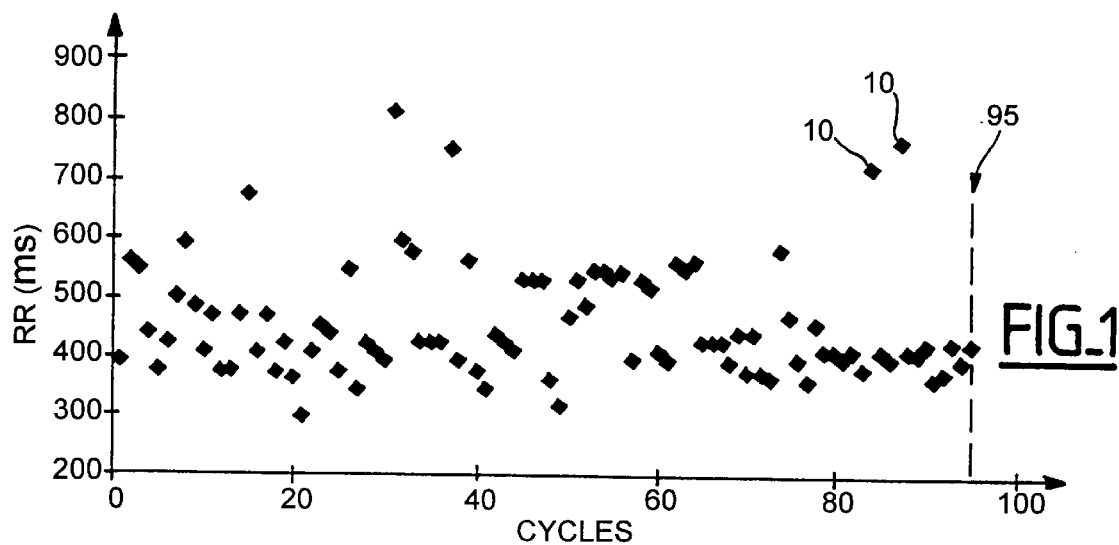
FIG_1
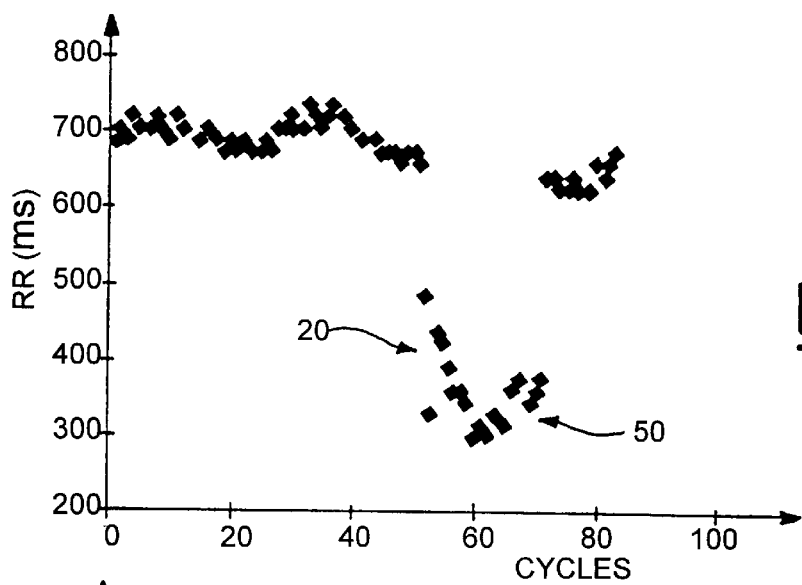
FIG_2
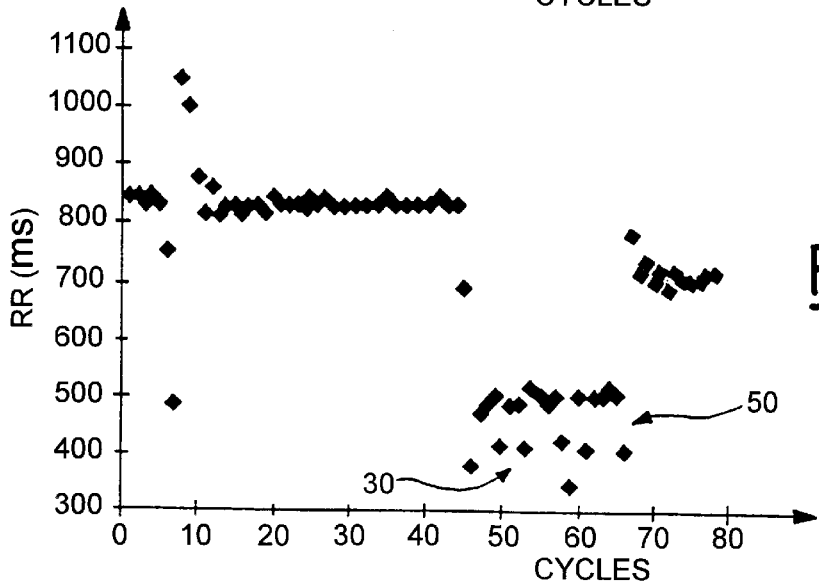
FIG_3

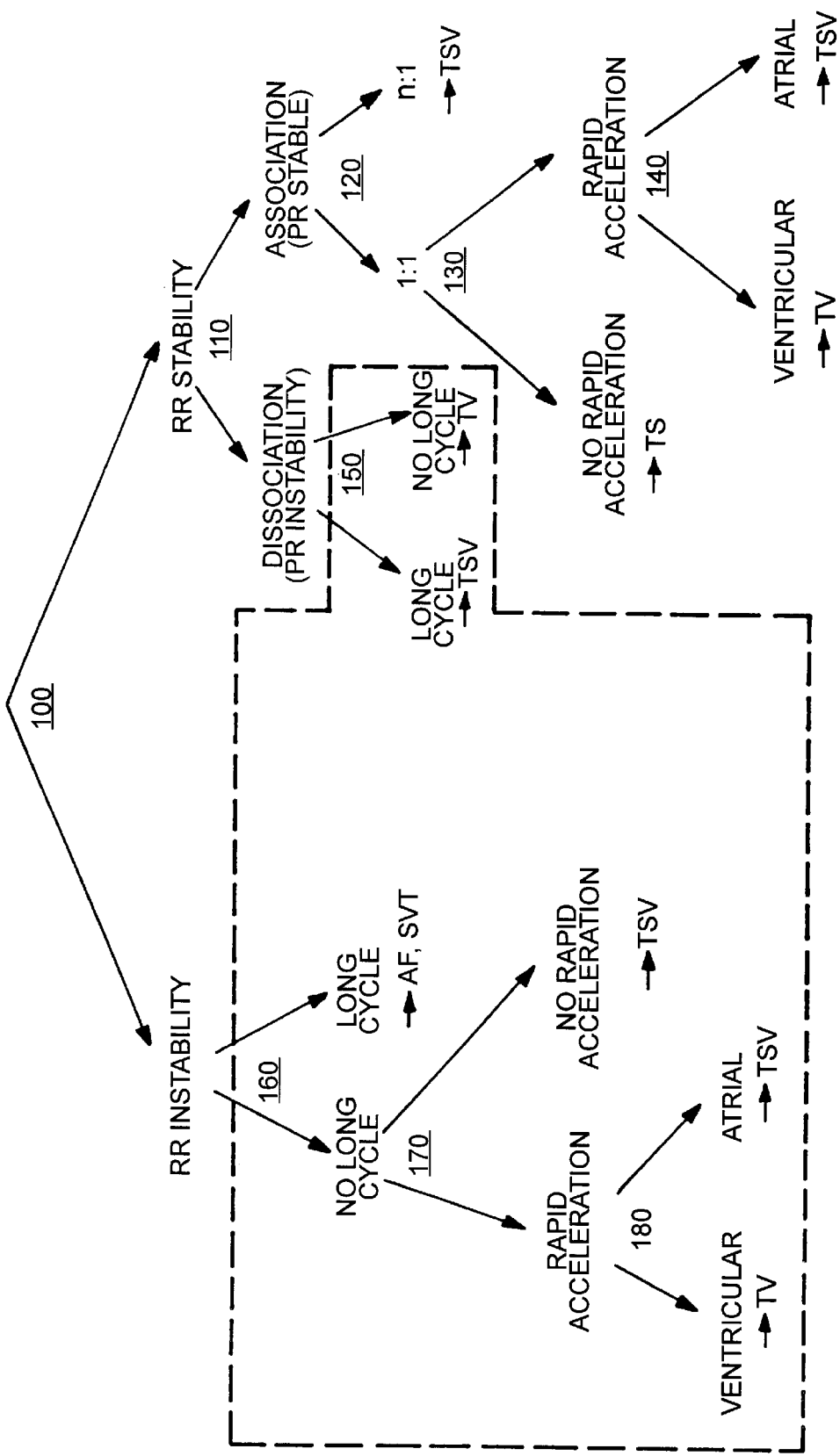
FIG_4 ns and Apparatus for Improved Tachycardia Discrimination in an Active Medical Device

FIELD OF THE INVENTION

The present invention concerns "active implantable medical devices" (such as those defined by the 20 Jun. 1990 directive 90/385/EEC of the European Community Council), and more particularly to the family of devices able to deliver to the heart electrical impulses of high energy (that is to say an energy significantly exceeding the energy provided for the simple stimulation) in order to terminate a tachyarrythmia (tachycardia). These high energy modes of therapy also include a stimulation mode programmed at a high frequency known as AntiTachycardica Pacing ("ATP"). Such devices are commonly called "implantable defibrillators" or "devices for cardioversion" (cardioverters), and in combination implantable cardioverter defibrillators ("ICDs"). It should be understood, however, that the invention also includes implantable defibrillators/cardioverters/pacemakers as well as implantable defibrillators/ pacemakers.

BACKGROUND OF THE INVENTION

These high energy devices include a pulse generator which monitors the cardiac activity in both the atrial and the ventricular cardiac chambers and generates pulses of stimulation energy (a "stimulation" pulse) or high energy (a "shock" pulse) when the heart presents a ventricular arrhythmia susceptible to be treated. When the shock pulse energy is between 0.1 and 10 J approximately, one designates this therapy under the name of "cardioversion" and the electrical shock is called a "cardioversion shock". When the shock pulse energy is greater than 10 J approximately, the therapy is called defibrillation and the electrical shock is called a "defibrillation shock".

This shock pulse therapy is desired to be delivered when one detects a ventricular tachycardia (VT), but only in the case that the detected tachycardia is a real VT, and not a supra-ventricular tachycardia (SVT). Indeed, in the latter case, the tachycardia is of atrial origin and the high energy shock pulse that would be delivered would not have any effect because the defibrillation electrode or, if appropriate, the stimulation electrode, is not found in the atrial region.

A tachyarrythmia (also known as a tachycardia) corresponds to an abnormal rapid cardiac rhythm, and includes ventricular fibrillation (VF), ventricular tachycardia (VT), sinus tachycardia (ST), and supra-ventricular tachycardia (SVT). The supra-ventricular tachycardia (SVT) includes atrial tachycardia (AT), atrial flutter and atrial fibrillation (AF).

The diagnosis of tachycardias can be performed, in any manner that is known (see for example, EP-A-0 626 182 and its corresponding U.S. Pat. No. 5,462,060, commonly assigned to ELA Medical, which U.S. Pat. No. 5,462,060 is incorporated herein by reference in its entirety), from criteria such as the ventricular frequency, the ventricular interval stability (the RR interval), the analysis of the atrial-ventricular association (as made be revealed by the stability of the PR interval) and the mode of beginning of the tachycardia (that is, the presence of an abrupt or rapid acceleration and the cavity of origin, ventricular or atrial).

More precisely, the device described in the aforementioned EP and U.S. patents defines that there is stability of the RR intervals when the peak of auto-correlation, divided by the total of auto-correlation, exceeds a determined ratio (the peak of auto-correlation is the maximal number of recent intervals in the ventricle that satisfying a predetermined stability criterion).

It also defines that there is conduction stability when the value of the peak of cross-correlation is divided by the value of the peak of auto-correlation (or, in an other embodiment by the total of cross-correlation) exceeds a determined reference (the peak of cross-correlation is the maximal number of intervals of conduction from the atrium that satisfy a predetermined stability criterion). In others words, in the first aforementioned case, one compares the stability of the conduction between the two cavities to those of intervals in the ventricle, while in the second case one expresses the stability of the conduction between the two cavities according to the presumed totality of conduction.

When there is no stability in the ventricle (that is, there are unstable RR intervals), that means that the tachyarrythmia is probably not susceptible to be interrupted by a therapy applied to the ventricle, and the process then determines that it is not susceptible to be interrupted in this cavity.

On the other hand, when there is stability in the ventricle (i.e., stable RR intervals), but not stability of conduction (i.e., an absence of atrial-ventricular association), that means that the tachyarrythmia probably has its origin in the ventricle, and the process determines that it is susceptible to be interrupted by a shock therapy applied to the ventricle.

Whenever there is stability in the ventricle (stable RR intervals), and also a conduction stability (established atrial-ventricular association), the process in question determines if the conduction from the second cavity is 1:1 or n:1. This is done by comparing the peak of cross-correlation to the total of cross-correlation. In the case of a 1:1 association, one considers another criterion, namely the presence or absence of an acceleration (rapid acceleration) originating with a dissociation, to determine whether or not the tachyarrythmia is susceptible to be interrupted by stimulation pulses and/or electrical shock pulses (cardioversion or defibrillation).

In the case of a n:1 association, one concludes that the tachyarrythmia is in no manner susceptible to be interrupted by stimulation of the ventricle, because the tachyarrythmia has its origin in the atrium.

One observes, however, in some cases, a clinical failure of the foregoing classification algorithm.

French patent application No. 96 07533 and its corresponding U.S. application Ser. No. 08/877039 filed Jun. 17, 1997, commonly assigned to the assignee hereof, ELA Medical, which US application is incorporated herein by reference in its entirety, described in this regard an improvement that allows one to detect the presence of long RR cycles so as to insure a supplementary discrimination between VT and SVT, especially in the presence an installed and conducted AF presenting regular RR intervals during a sufficiently long duration, to conclude a false diagnosis of VT (regular rhythm and dissociation between atrium and ventricle). However, the clinical observation reveals that, in some cases of tachyarrhythmias really necessitating a therapy, this therapy has not been applied, or it has been applied too late. These particular cases will now be explained with reference to FIGS. 1 to 3, that represents the evolution of the value of the RR intervals (a "short" RR interval corresponds to a high ventricular rhythm) over the course of a succession of such cycles.

In the case illustrated in FIG. 1, the RR intervals rapidly become very stable, with a typical difference of 63 ms between the minimal value and the maximal value for the seventeen cycles preceding the shock therapy, which is applied on the $n^{th}$ cycle 95. The algorithm has indeed interpreted this situation as corresponding to a stability of RR intervals with an absence of association, resulting in a diagnosis of VT, which is normally susceptible to shock therapy.

Nevertheless, the presence of a long RR cycle at 10 indicates, in a manner clear to the clinician, that it does not concern a VT, but rather an SVT, which is not reducible by a shock therapy. One sees, in this example, that the classification of the prior art device has produced a false positive diagnosis (an indication of a VT, although it actually concerned an SVT).

In the cases of FIGS. 2 and 3, conversely, a progressive variation of the RR interval (at 20 on FIG. 2), or an instability of the RR interval over very short cycles (at 30 on FIG. 3), has been interpreted by the classification of the prior art device as an instability of the RR rhythm, thus concluding wrongly at 50 that it was not necessary to apply a therapy. In these examples, the criterion to diagnose and process a VT was the detection of at least six cycles in the peak of autocorrelation (defining the RR interval stability) during eight continuous cycles while, in the cases of FIGS. 2 and 3, the duration of persistence of the RR stability had not exceeded five and six cycles, respectively.

In these two latter examples, one has therefore reached a false negative diagnosis, that is to say the device classification concluded an SVT existed although it really concerned a VT.

OBJECTS AND SUMMARY OF THE INVENTION

It is therefore, an object of the invention to remedy the aforementioned disadvantages, by proposing to improve existent devices so as to minimize further any risk of false diagnosis of VT (false positive or false negative) in some atypical situations. It is another object to increase the specificity and the reliability of the analysis of tachyarrhythmias.

The medical device of the invention is a defibrillator or cardiovertor of a type well known, such as is described, for example, in aforementioned EP-A-0 626 182. One such device comprises:

means for delivering a shock therapy (i.e., a delivery of a defibrillation, cardioversion, or antitachycardia stimulation (ATP) to shock the ventricle and/or the atrium, as may be appropriate in the circumstances);

means for collecting (i.e., sensing or monitoring) the atrial and ventricular activity;

means for suspecting the presence of tachycardia episodes in the collected activity, these means comprising means for analyzing the stability of RR intervals and the stability of associated PR intervals;

means of classification, able to discriminate tachycardias detected as between ventricular tachycardias and supraventricular tachycardias; and means for, selectively, (i) commanding delivery of a therapy in the presence of a classified ventricular tachycardia or (ii) inhibiting delivery of a therapy in the presence of a classified supra ventricular tachycardias, and optionally, releasing a suitable atrial therapy.

According to the invention, the classification means further comprises means for determining the presence or the absence of a rapid acceleration of the RR interval rhythm, and for determining, if necessary, the chamber of origin (atrial or ventricular) of such acceleration, which means are operating in the case of the detection of unstable RR intervals.

Preferably, means able to determine the presence or the absence of a rapid acceleration operates in the case of the detection of unstable RR intervals with an absence of long RR intervals detected during the period of analysis.

More preferably this classification means further comprises means for determining the presence or the absence of long RR intervals in a given period of analysis, in the case of detection of stable RR intervals with unstable PR intervals.

BRIEF DESCRIPTION OF THE DRAWINGS

Other characteristics and advantages of the present invention will appear to a person of ordinary skill in the art, in view of the following detailed description, made with reference to the drawings annexed, in which:

FIGS. 1 to 3, as aforementioned, are chronograms representative of clinical statements of variations of the RR rhythm over the course of a certain number of cycles having resulted in a false positive diagnosis (FIG. 1) or false negative diagnosis (FIGS. 2 and 3) using the prior art classification; and FIG. 4 is a flow chart of the process for the discrimination and the classification of tachyarrhythmias in accordance with a preferred embodiment of the invention.

DETAILED DESCRIPTION OF THE DRAWINGS

With reference to FIG. 4, one has represented in a schematic manner a flow chart of the process for the detection and classification of tachyarrhythmias of a defibrillator, such as the commercial model Defender 9001 of ELA Medical, which process algorithm has been improved according to the teaching of the present invention. More precisely, the part of the flow chart enclosed in a dashed frame corresponds to the improvement of the present invention, while the rest of the flow chart corresponds to elements of the classification already known and described in the aforementioned EP-A-0 626 182 and U.S. Pat. No. 5,462,060, to which one can refer for further details. It should be understood that the device of the present invention is a microprocessor-based active implantable medical device having memory and programming that implements in software the functions of the process, including the improvements, disclosed herein, and leads to delivering the appropriate shock energy to the desired cardiac chamber.

With reference to FIG. 4, the first stage of the analysis (test 100) determines whether or not one has a stability of the rhythm RR. If there is RR stability, one proceeds then to the examination (stage 110) of the presence or absence of an atrio-ventricular association.

If there is association, then at test 120, one examines if it concerns an association of 1:1 or n:1. In the latter case, one considers that there is an SVT and inhibits all therapy action on the ventricle. Preferably, one can release a therapy action on the atrium (if atrial therapy is provided by the device).

In the case of a 1:1 association, one determines (test 130) whether or not there has been a rapid acceleration the rhythm. The criterion for analysis of the acceleration of the ventricular rhythm and the determination of the origin of this acceleration are described in EP-A-0 626 182 and the counterpart U.S. Pat. No. 5,462,060 aforementioned. For example, an acceleration criterion may be applied in which the ventricular rate acceleration is compared to a preset limit, which may be a programmable value, and is preferably approximately 25%, and if the limit is exceeded, the rate is determined to be rapid.

If there has been little or no acceleration ("non rapid" acceleration), one considers that the tachycardia is a sinus tachycardia (ST), probably physiological origin, and one inhibits all action on the ventricle.

If, on the other hand, there is a rapid acceleration of RR interval, one determines (test 140) the origin of this acceleration: if ventricular in origin, then the tachycardia concerns a VT and one authorizes a therapy action on the ventricle; if atrial in origin, then the tachycardia concerns an SVT, one inhibits all action on the ventricle, and one releases eventually a therapy action on the atrium.

The part of the flow chart just described is implemented by the classification algorithm of the prior art.

In the case where, at the test 100, one detected an unstable RR rhythm, the algorithm of the prior art systematically considered that there is an SVT and inhibited all action on the ventricle. It was similarly the case where, at the test 110, one detected an absence of association in the presence of stable RR intervals. As explained above, this could result in the false diagnosis in some non-typical clinical situations.

As a solution to this, the invention proposes, in these cases, to examine the possible presence of long RR intervals, so as to improve the classification of tachyarrhythmias. Thus, in the case where, at the test 110, one had detected an absence of association, one proceeds to a supplementary discrimination (test 150) to detect the presence or the absence of long RR cycles.

The criterion "presence of a long RR cycle" is defined as being satisfied if one detects at least one cycle whose RR interval duration is greater than a predetermined reference value. It can concern, in particular, a duration that one can express under the form RRmax+StabRR; RRmax being the maximum limit of the peak of auto-correlation (defining the stability of RR interval), and StabRR being a programmable value defining a "gap" interval (interval of separation) between the high limit and the detection range of the RR intervals considered to be long.

If there is the presence of a long cycle, one considers that there is a SVT, inhibits all action on the ventricle, and releases eventually an action on the atrium.

Thus, in the example FIG. 1, one inhibits the application of a shock therapy after the occurrence of a long cycle 10, thereby avoiding a false positive detection.

On the other hand, if one does not detect a long RR cycle, then one considers that there is VT and authorizes an action on the ventricle.

If, at the test 100, one detects an instability of the RR rhythm, one proceeds to a supplementary discrimination (test 160) to determine, as in the test 150, the presence or the absence of a long RR cycle.

The presence of a long RR cycle reveals an atrial fibrillation (AF), that is to say an abnormally high frequency of the atrial rhythm conducted to the ventricle. An atrial fibrillation is a particular form of SVT. This implies that one inhibits all action on the ventricle, because an action on the ventricle would be without effect, and could be dangerous to the patient.

In the case where, on the other hand, one does not detect a long cycle, one determines (test 170) whether or not there has been a rapid acceleration of the RR rhythm, in the same manner as the test 130. The absence of a rapid acceleration reveals that the tachyarrhythmia concerns an SVT, and one therefore has to inhibit all action on the ventricle.

In the presence a rapid acceleration, one then determines its origin (test 180, operated in the same manner as the test 140). If the acceleration comes from the atrium, the tachyarrhythmia concerns an SVT and one inhibits all action on the ventricle. On the other hand, if the acceleration finds its origin in the ventricle, the tachyarrhythmia concerns a VT, and one allows a shock therapy action on the ventricle.

One thus avoids detecting the false negative diagnosis of the examples illustrates in FIGS. 2 and 3, by allowing the deliverance of a therapy despite the instability of the RR rhythm at 20 and 30 respectively.

In an alternative embodiment of the invention, one can omit the test 160, that is to say that, in case of a determined unstable RR interval, one proceeds directly to the acceleration test (test 170), without determining in this case whether or not there is the presence of a long RR cycle.

One skilled in the art will appreciate that the present invention can be practiced by other than the disclosed embodiments, which are presented only for purposes of illustration and not of limitation.

We claim:

1. An implantable medical device of the defibrillator/cardiovertor type having:
   means for delivering a shock therapy;
   means for monitoring atrial and ventricular activity;
   means for suspecting the presence of a tachycardia episode in the monitored activity;
   means for analyzing the stability of RR intervals and the stability of associated PR intervals during a period of analysis;
   means of classification operable to discriminate a suspected tachycardia episode as between a ventricular tachycardia and a supra-ventricular tachycardia, and
   means for, selectively, (i) commanding a therapy delivery in response to a classified ventricular tachycardia or (ii) inhibiting a therapy delivery in response to a classified supra-ventricular tachycardia, wherein the improvement comprises:
   a means for determining a presence of a rapid acceleration of the RR interval rhythm, and
   means, responsive to a determined unstable RR interval, for determining a chamber of origin of the acceleration, wherein said classification means discriminates suspected tachycardias based on at least one of said determined rapid acceleration and said determined chamber of origin.

2. The device of claim 1, wherein the means for determining the presence of a rapid acceleration is operated in response to a detection of unstable RR intervals and the absence of long RR intervals detected in the period of analysis.

3. The device of claim 1, in wherein the classification means further comprises means for determining the presence of long RR intervals in the period of analysis, in response to a detection of stable RR intervals with unstable PR intervals.

4. The device of claim 1 wherein the classification means further comprises means for discriminating a suspected tachycardia episode as between a ventricular tachycardia and a supra-ventricular tachycardia according to a predetermined criteria and a given adjustment of said predetermined criteria and means for modifying said discrimination operation, in response to a supra-ventricular tachycardia, by one of adding temporarily at least one criterion and modifying temporarily the adjustment of a predetermined criterion.

5. The device of claim 4, wherein the added criterion further comprises a supplementary research criterion of at least one of a short RR interval range and a long RR interval range, said one RR interval range being significantly distanced from a RR interval stability zone.

6. A method for discriminating tachycardia episodes in an active implantable medical device of the defibrillator/cardiovertor type for delivering a shock therapy, comprising:

monitoring atrial and ventricular activity;

identifying a tachycardia episode occurring in the monitored activity;

analyzing the stability of the RR interval, determining the stability of the RR intervals and, in response to a determined unstabled RR interval, determining a chamber of origin of a determined rapid acceleration;

classifying said tachycardia episode as between one of a ventricular tachycardia and a supra-ventricular tachycardia according to the RR interval stability; and authorizing delivery of a shock therapy in response to a classified ventricular tachycardia and inhibiting delivery of a shock therapy in response to a classified supra-ventricular tachycardia;

wherein said classification step further comprises, in response to a determined RR instability, determining the presence of a long RR cycle during a preselected number of RR interval cycles, and reclassifying the classified tachycardia episode as one of an atrial tachycardia in response to the presence of a long RR cycle and a suspected ventricular tachycardia in response to an absence of a long RR cycle.

7. The method of claim 6, wherein the classifying step further comprises testing, in response to a suspected ventricular tachycardia, whether there is a rapid acceleration of RR intervals during said preselected number of RR intervals, and determining that the suspected ventricular tachycardia is a supra-ventricular tachycardia in response to a determined absence of a rapid acceleration, and a possible ventricular tachycardia in response to a determined rapid acceleration.

8. The method of claim 7, wherein the classifying step further companies determining, in response to a determined possible ventricular tachycardia, the chamber of origin of the acceleration, and determining that the possible ventricular tachycardia is a supra-ventricular tachycardia in response to the atrial chamber being the chamber of origin.

9. The method of claim 6 further comprising authorizing an atrial therapy in response to a classified supra-ventricular tachycardia.

* * * * *

UNITED STATES PATENT AND TRADEMARK OFFICE
CERTIFICATE OF CORRECTION

PATENT NO.   : 5,868,793
DATED        : February 9, 1999
INVENTOR(S)  : Remi Nitzsche It is certified that error appears in the above-identified patent and that said Letters Patent is hereby corrected as shown below:

Column 1,
Line 61, delete "made" and insert -- may -- therefor;

Column 2,
Line 3, delete "satisfying" and insert -- satisfied -- therefor;
Line 5, delete "that there is conduction stability" and insert -- conduction stability as being -- therefor;
Line 54, delete "presence an" and insert -- presence of an -- therefor;

Column 3,
Line 63, delete "supra ventricular tachycardias" and insert -- supra-ventricular tachycardia -- therefor;

Column 4,
Line 61, delete "acceleration the" and insert -- acceleration of the -- therefor;

Column 5,
Line 10, delete "interval" and insert -- intervals -- therefor;
Line 46, delete "example" and insert -- example represented by -- therefor;

Column 6,
Line 3, delete "presence" and insert -- presence of -- therefor.

Signed and Sealed this

Twenty-first Day of June, 2005

JON W. DUDAS
*Director of the United States Patent and Trademark Office*